United States Patent
Hiroi et al.

(10) Patent No.: US 8,121,395 B2
(45) Date of Patent: Feb. 21, 2012

(54) INSPECTION APPARATUS AND AN INSPECTION METHOD FOR INSPECTING A CIRCUIT PATTERN

(75) Inventors: Takashi Hiroi, Yokohama (JP); Takeyuki Yoshida, Hitachinaka (JP); Naoki Hosoya, Tokyo (JP); Toshifumi Honda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 415 days.

(21) Appl. No.: 12/393,827

(22) Filed: Feb. 26, 2009

(65) Prior Publication Data

US 2009/0226075 A1    Sep. 10, 2009

(30) Foreign Application Priority Data

Mar. 7, 2008 (JP) ................................. 2008-057153

(51) Int. Cl.
*G06K 9/00* (2006.01)
(52) U.S. Cl. ...................................................... 382/145
(58) Field of Classification Search .................. None
See application file for complete search history.

(56) References Cited

U.S. PATENT DOCUMENTS

| 5,173,719 A | 12/1992 | Taniguchi et al. |
| 5,502,306 A | 3/1996 | Meisburger et al. |
| 6,347,150 B1 | 2/2002 | Hiroi et al. |
| 7,424,146 B2 * | 9/2008 | Honda et al. ................. 382/149 |

FOREIGN PATENT DOCUMENTS

| JP | 5-258703 | 10/1993 |
| JP | 10-89931 | 4/1998 |
| JP | 2001-091228 | 4/2001 |

OTHER PUBLICATIONS

Okuda, Hirohito et al., "Robust Defect Detection Method Using Reference Image Averaging for High Throughput SEM Wafer Pattern Inspection System," SPIE vol. 6152 61524F-1, 2006.
Japanese Office Action issued in Japanese Patent Application No. JP 2008-057153 dated Jul. 20, 2010.

* cited by examiner

*Primary Examiner* — Tu Nguyen
(74) *Attorney, Agent, or Firm* — McDermott Will & Emery LLP

(57) ABSTRACT

A circuit-pattern inspection apparatus and related method provide a highly sensitive defect inspection of an area including the most circumferential portion of a memory mat of a semiconductor chip formed on a semiconductor wafer. In certain examples, an image of a circuit pattern of a die formed on the semiconductor wafer is acquired to judge whether or not the circuit pattern contains a defect.

4 Claims, 13 Drawing Sheets

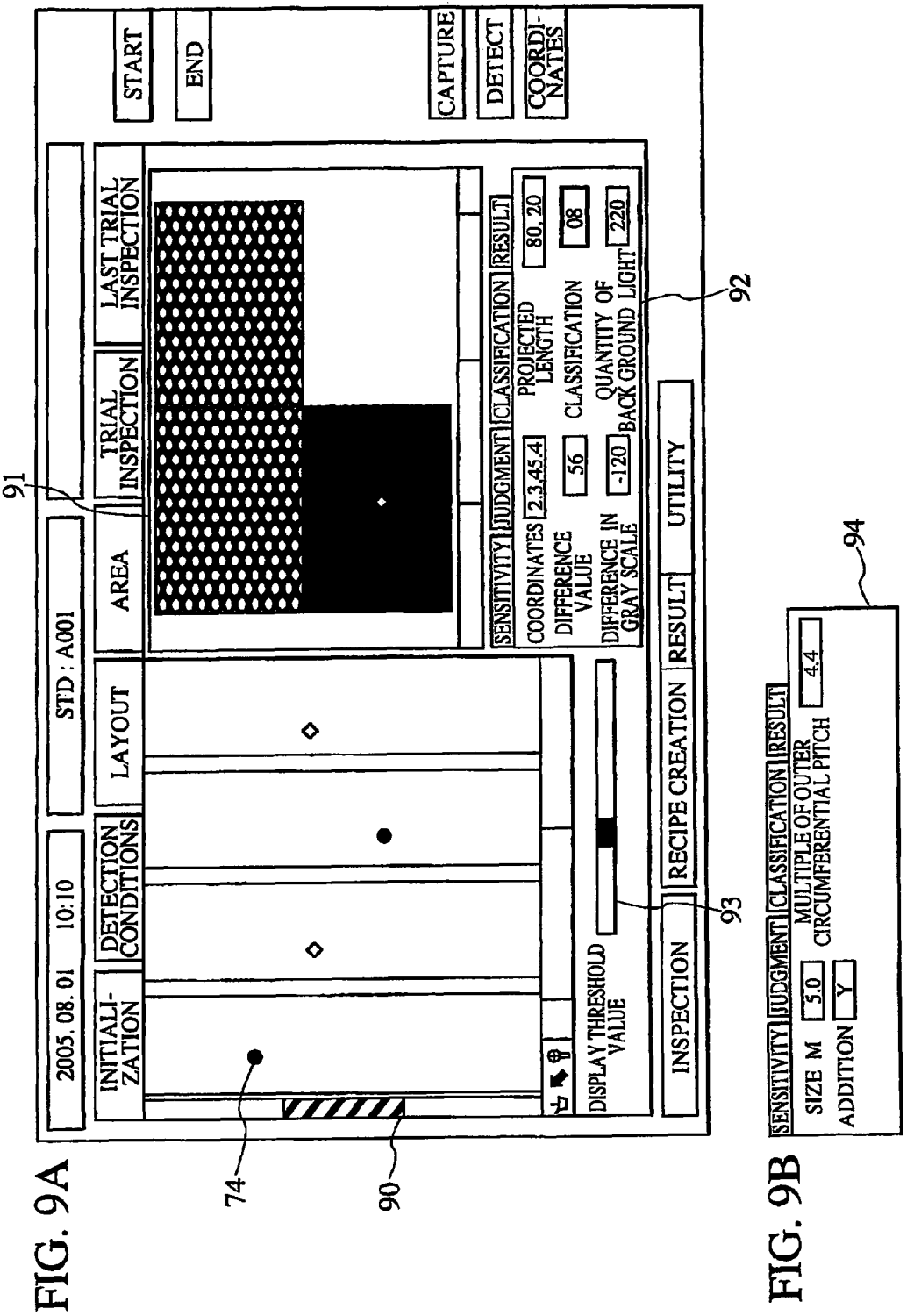

110  111  112  113

INSPECTION APPARATUS AND AN INSPECTION METHOD FOR INSPECTING A CIRCUIT PATTERN

FIELD OF THE INVENTION

The present invention relates to an inspection apparatus, and an inspection method, for inspecting, with an electron beam or a light beam, a substrate having a circuit pattern used in a semiconductor device and a liquid crystal.

BACKGROUND OF THE INVENTION

An inspection apparatus, which uses an electron beam, irradiates a target semiconductor wafer to be inspected with an electron beam, and detects a secondary electron generated therefrom. The inspection apparatus then creates an image from the detected secondary electron so as to detect a defective semiconductor wafer. In order to create a fine structure image, an electron beam is thinly converged with an electron lens, and the electron beam is then scanned over a semiconductor wafer to acquire a secondary electron image. Next, the-thus detected secondary electron image is compared with a reference image having the same pattern. An area in which the difference between these images is large, or a position at which the difference between these images is large, is judged to be a defect (refer to, for example, Japanese Unexamined Patent Application Publication No. JP05-258703A1).

Since such a method for inspecting the whole surface of a semiconductor wafer requires an extremely long period of time for inspection, it cannot be used for monitoring manufacturing processes. As a measure for such a drawback, a technique for shortening the inspection time is known (refer to, for example, Japanese Unexamined Patent Application Publication No. JP10-089931A1). According to this technique, if a target wafer includes a plurality of patterns in which an area having the two-dimensional repeatability of a semiconductor wafer and an area having the repeatability only in an X direction or a Y direction coexist, a cross comparison is made between an attention point and a comparison point that is apart from the attention point by a repeated pitch. Only an area in which there is the difference from the attention point and the comparison point is extracted as a defect candidate, thereby shortening the inspection time. In addition, noise reduction by a RIA (Reference Image Averaging) technique is also known; the RIA technique averages an image including a defect, and a reference image that does not include a defect (refer to non-patent literature 1 titled "Robust Defect Detection Method Using Reference Image Averaging for High Throughput SEM Wafer Pattern Inspection System" by H. Okuda et al., SPIE Vol. 6152 61524F-1 (2006)).

The number of functions per unit area of a circuit pattern to be inspected by an inspection apparatus has increased four times in the past three years. This increase is achieved by the miniaturization of a pattern. Accordingly, if a defect is minute, it is difficult to discriminate the defect from noises included in a signal of a normal pattern. As a result, it is difficult to make a defect detect that will be achieved when a difference between a defective pattern and a normal pattern is calculated. For example, a memory mat of a memory device is subjected to ultimate pattern miniaturization because one memory cell is assigned to one memory bit for the memory mat. Even if a minute defect on a memory mat cannot be detected, the device normally operates as a whole. The miniaturization of the memory mat is further accelerated by use of the redundant circuit technique. In contrast, if peripheral circuits other than memory mats have one failure in a device, the device will become defective. Therefore, to prevent a defective part relating to peripheral circuits from occurring and to detect defects that may be produced without fail, the pattern size of a peripheral circuit is not so miniaturized in comparison with that of a memory mat. Therefore, when the distribution of positions at which a pattern defect has occurred is referred to, the memory mat is higher in a defect occurrence ratio than the peripheral circuit. In particular, because the pattern density rapidly changes in the most circumferential portion of the memory mat, due to a deviation from the design size at the time of exposure or the like, manufacture of the devices is extremely difficult. As a result, a rate of occurrence of a pattern defect is disadvantageously very high.

Because a die having a plurality of identical patterns is formed on a semiconductor wafer, the conventional inspection apparatuses adopt a die comparison method in which die patterns are compared with each other. The die comparison method has the advantage that the whole die can be subjected to defect judgment. However, because a comparison is made between patterns that are apart from each other by about 10 mm on a wafer and the formed patterns are different from each other, the defect judgment performance may somewhat decrease in the die comparison method.

On the other hand, the conventional inspection apparatuses adopt a cell comparison method in which a comparison is made between patterns that are apart from each other by repeated pitch. This cell comparison method takes advantage of the repeatability of a memory mat. Because the cell comparison method uses the repeatability, the cell comparison method has the disadvantage that a peripheral circuit having no repeatability, and an edge portion of the repetition, cannot be inspected. However, because a comparison is made between areas that are apart from each other only by repeated pitch, the similarity of a pattern is very high, which makes it possible to achieve the defect judgment with high sensitivity. This is the advantage of the cell comparison method. On the other hand, in the cross-comparison method in which comparisons are made in a plurality of directions using the repeatability, inspection is performed on the basis of the repeatability including an area having no repeatability. Therefore, many normal portions each having no repeatability are output as defect candidate points. This requires an image processing system to have high throughput and it cannot be said that sufficient consideration is made in terms of performance. Under these circumstances, although highly sensitive inspection of an area including the most circumferential portion of a memory mat is indispensable, these points are not sufficiently considered for the conventional inspection apparatuses.

SUMMARY OF THE INVENTION

An object of the present invention is to provide an inspection apparatus, and an inspection method, which are capable of making a highly sensitive defect judgment of an area including the most circumferential portion of a memory mat of a semiconductor chip formed on a semiconductor wafer.

In order to solve the above-described problems, according to one aspect of the present invention, there is provided a circuit-pattern inspection method in which an image of a circuit pattern of a die formed on a semiconductor wafer is acquired to judge whether or not the circuit pattern has a defect, the circuit-pattern inspection method comprising the steps of:

on the basis of the repeatability of the circuit pattern, distributing data of the image to a plurality of image memories, and storing the data therein;

comparing the data of the image stored in the image memories with a combined reference image to generate a difference image, the combined reference image being combined by adding and averaging in a direction of the repeatability;

judging that an area in which a difference value of the difference image is larger than a predetermined threshold value is a defect; and integrating and outputting a plurality of pieces of defect information, the defect information including image data judged to be defective and coordinates indicative of the defect.

In addition, when a memory cell is judged to be defective in a corner portion of a rectangular area of a memory mat having a plurality of memory cells in the circuit pattern of the die, this memory cell is not treated as a defect.

According to the present invention, it is possible to provide a circuit-pattern inspection apparatus, and a circuit-pattern inspection method, which is capable of highly sensitive defect judgment of an area including an outermost circumferential portion of a memory mat.

BRIEF DESCRIPTION OF THE DRAWINGS

Other objects and advantages of the invention will become apparent from the following description of embodiments with reference to the accompanying drawings in which:

FIGS. 9A, 9B are diagrams each illustrating, as an example of GUI, a screen in which defect information is displayed;

DETAILED DESCRIPTION OF THE PREFERRED EMBODIMENTS

Embodiments of the present invention will be described below with reference to accompanying drawings. Although a circuit-pattern inspection apparatus which uses an electron beam is taken as an example in the description below, procedures for image comparison processing and defect judgment processing thereof will be omitted because the circuit-pattern inspection apparatus operates in a manner similar to an optical inspection apparatus for optically inspecting a circuit pattern.

First Embodiment

A first embodiment of the present invention will be described below with reference to accompanying drawings.

Figure 1:
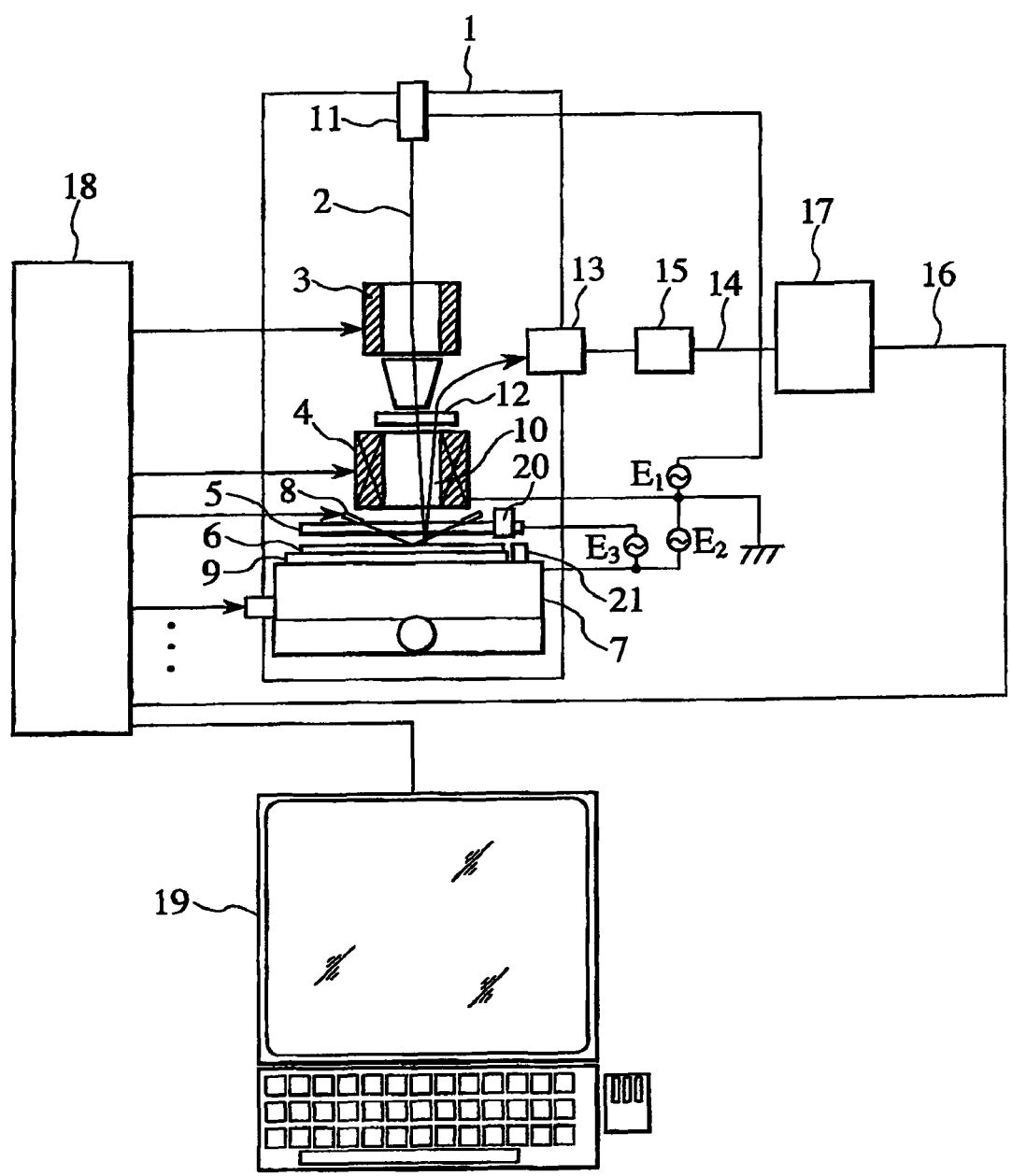
FIG. 1 is a diagram illustrating an overall configuration of a circuit-pattern inspection apparatus.

FIG. 1 is a diagram illustrating an overall configuration of a circuit-pattern inspection apparatus. In FIG. 1, the circuit-pattern inspection apparatus is an apparatus which uses a scanning electron microscope, and is configured mainly as follows. An electronic optical column 1 is maintained under vacuum. An electron source 11 generates an electron beam 2. A deflector 3 deflects the electron beam 2. An objective lens 4 converges the electron beam 2. A charge control electrode 5 controls the field intensity. An XY stage 7 moves a semiconductor wafer 6 having a circuit pattern in an XY direction. A height sensor 8 measures the height of the semiconductor wafer 6. A sample stage 9 holds the semiconductor wafer 6. A converging optical unit 12 converges a secondary signal 10 such as a secondary electron and a backscattered electron. The secondary signal 10 occurs when the semiconductor wafer 6 is irradiated with the electron beam 2. A sensor 13 detects a secondary signal. An A/D converter 15 converts a signal detected by the sensor 13 into a digital signal 14. A defect judgment unit 17 subjects the digital signal 14 to image processing to extract defect information 16. A total control unit 18 receives the defect information 16 transmitted from defect judgment unit 17 and controls the circuit-pattern inspection apparatus as a whole. The total control unit 18 includes a microprocessor and a memory. 19A denotes a console through which an instruction by a user is given to the total control unit 18, and on which information about the circuit-pattern inspection apparatus and that about a defect are displayed. An optical microscope 20 takes an optical image of the semiconductor wafer 6. A standard sample piece 21 is positioned at the substantially same height as the semiconductor wafer 6 so that electronic optical conditions can be closely adjusted.

Incidentally, although control signal lines from the total control unit 18 are partially omitted for the sake of simplification of the figure, the total control unit 18 is configured to be capable of controlling all elements of the circuit-pattern inspection apparatus. In addition, the following elements are not shown: a convergent lens which functions in conjunction with the objective lens 4 so that the electron beam 2 is thinly converged; a deflector for changing a trajectory of the secondary signal 10 generated in the semiconductor wafer 6; a vacuum exhaust unit for maintaining the electronic optical column 1 under vacuum; and a transfer unit for transferring the semiconductor wafer 6 from the outside to the inside of the electronic optical column 1.

Figure 2:
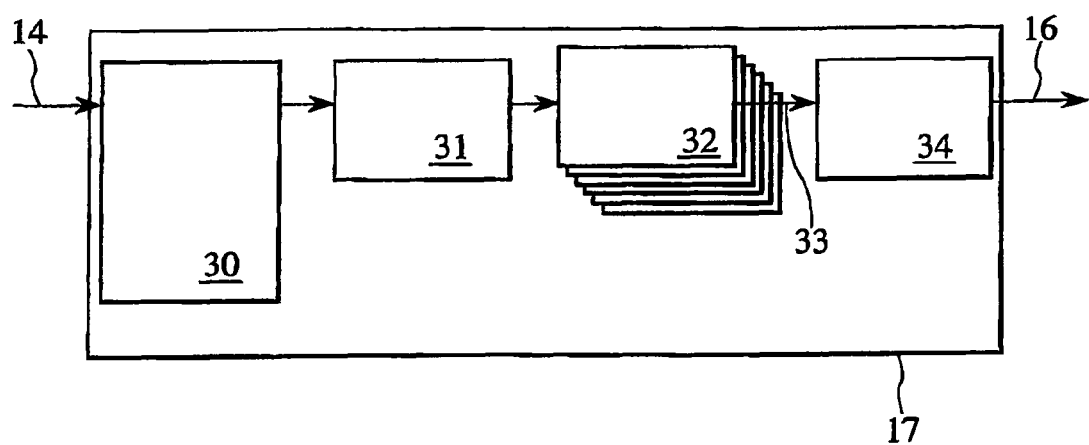
FIG. 2 is a functional block diagram illustrating signal processing performed in a defect judgment unit.

FIG. 2 is a functional block diagram illustrating. signal processing performed in the defect judgment unit 17. The digital signal 14 represents a series of digital values. The defect judgment unit 17 handles the digital signal 14 as a two-dimensional digital image. The defect judgment unit 17 is constituted of: an arithmetic element such as a microprocessor, a LSI (Large Scale Integration), and a FPGA (Field Programmable Gate Array); and a memory. According to an embodiment of the present invention, the defect judgment unit 17 includes: an image memory 30 for storing the digital signal 14; an image distribution unit 31 for distributing a digital image stored in the image memory 30 on the basis of area information; a plurality of PEs (Processor Element) 32, each of which handles each partial distributed image information so as to judge whether or not a defect exists in each partial area; and an information integration unit 34 for integrating pieces of partial defect information 33 handled by the plurality of PEs 32, and then for outputting defect information 16.

Figure 3A:
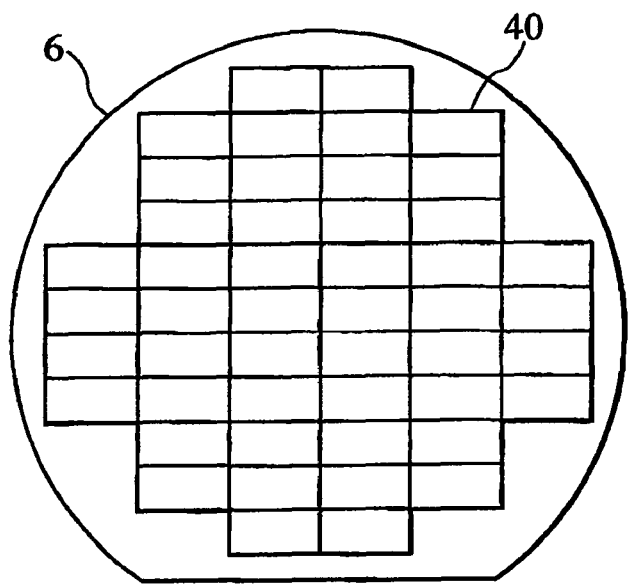
FIGS. 3A through 3D are plan views each illustrating a semiconductor wafer.
Figure 3B:
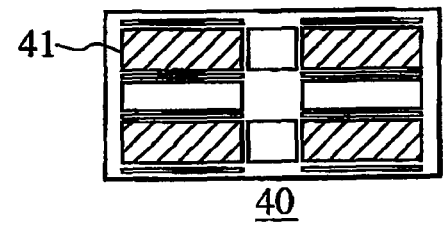
Figure 3C:
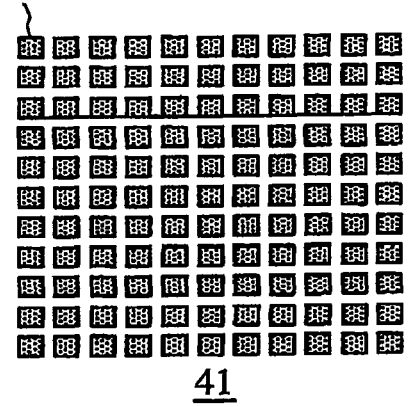
Figure 3D:
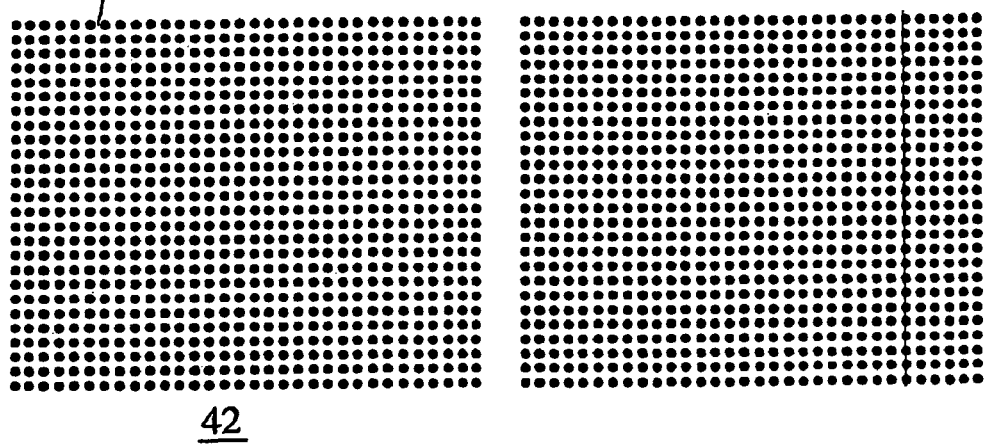

FIGS. 3A through 3D are plan views each illustrating a semiconductor wafer. As shown in FIG. 3A, the semiconductor wafer 6 has a disk shape having a diameter of from 200 mm to 300 mm and a thickness of about 1 mm. A large number of products are formed on the surface of the semiconductor wafer 6 at a time. The number of products ranges from several hundred to several thousand. For purposes of simplification, the figure illustrates semiconductor chips, each of which is called a "die", with the size of each semiconductor chip enlarged. As shown in FIG. 3B, a circuit pattern is formed in one rectangle (this rectangle is designated as a die 40) corresponding to one product. In the case of a general memory device, a pattern layout of the die 40 is constituted of, for example, four memory mat groups 41. As shown in FIG. 3C, each of the memory mat groups 41 is constituted of memory mats 42, the number of which is about 100×100. Moreover, as shown in FIG. 3D, each of the memory mats 42 is constituted of memory cells 43 that have the repeatability in a two-dimensional direction. The number of the memory cells 43 is several million.

Figure 4A:
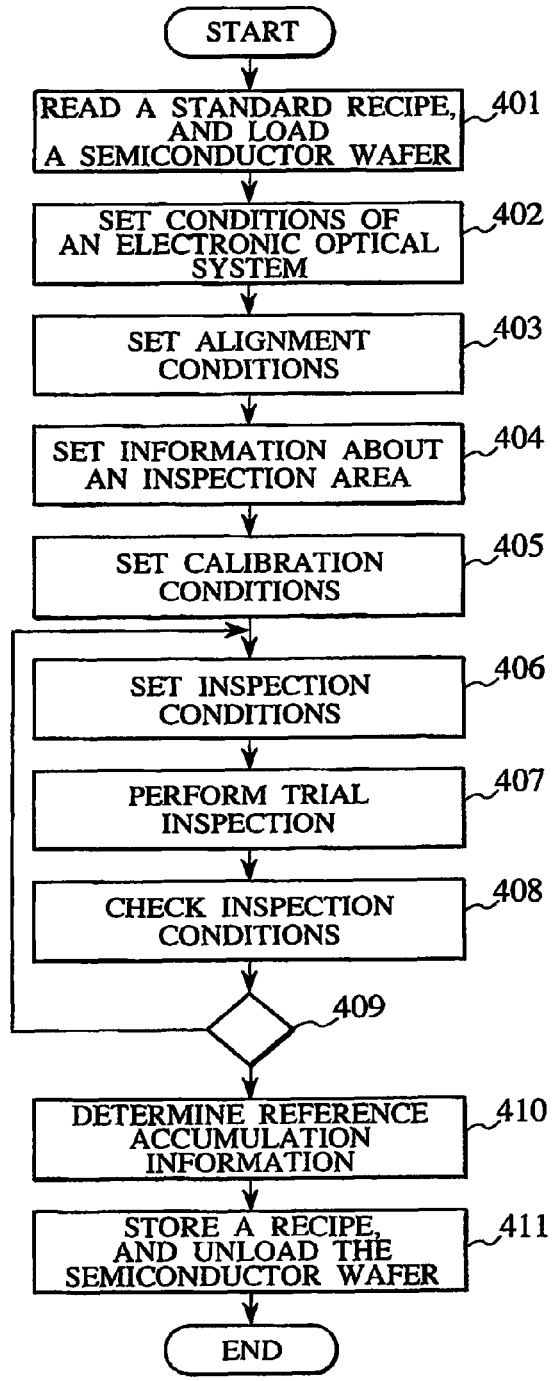
FIGS. 4A, 4B are flowcharts each illustrating steps executed when a circuit-pattern inspection apparatus is used.
Figure 4B:
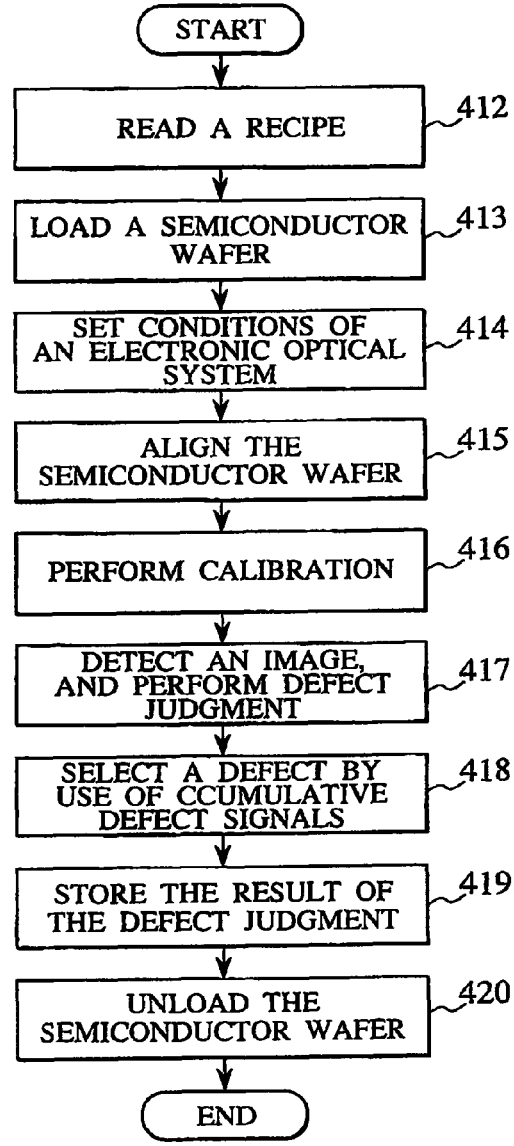

FIGS. 4A, 4B are flowcharts each illustrating steps executed when a circuit-pattern inspection apparatus is used. Steps of creating a recipe used to determine inspection steps and conditions will be described with reference to FIG. 4A and FIG. 1. First, an operator gives an instruction through a console 19 shown in FIG. 1 to allow the total control unit 18 to read a predetermined standard recipe, and then to load the semiconductor wafer 6 onto the sample stage 9 (step 401). Next, conditions of an electronic optical system are set (step 402). Specifically, the conditions of the electron optical system includes, for example, control values used to control the electron source 11, the deflector 3, the objective lens 4, the charge control electrode 5, the converging optical unit 12, the sensor 13, and the A/D converter 15. An image of the standard sample piece 21 is generated and then the control values which are set in the standard recipe are corrected so that desired values are acquired.

Next, a pattern used for alignment and coordinates thereof are registered to set alignment conditions (step 403). For example, the semiconductor wafer is formed with a pattern whose coordinates are known used to align the semiconductor wafer 6. Thus, the coordinates are inputted. In another case, four dies which are close to the circumferential edge of the semiconductor wafer 6 shown in FIG. 3A are selected. The alignment pattern formed in the die is specified on a wafer map that is a schematic diagram of the semiconductor wafer 6 displayed on a screen of the console 19.

Next, information about an inspection area, which is a target to be inspected, is set (step 404). The quantity of a detection light beam varies on a semiconductor wafer basis. Therefore, in order to perform inspection under specific conditions, an initial gain and a calibration coordinate point are set by selecting a coordinate point at which an image suitable for the calibration of the quantity of the detection light beam is acquired (step 405). Next, the operator uses the console 19 to select an inspection area, the pixel size, and the number of times addition is performed so that these conditions are set in the total control unit 18 (step 406). A method for specifying the inspection area is as follows. For example, an image of the standard sample piece 21, or a rectangle area in a schematic diagram of the semiconductor wafer, which is displayed on the screen of the console 19, is dragged with a mouse of a personal computer as described in FIGS. 12 through 14 in Japanese Unexamined Patent Application Publication No. JP10-162143A1. For example, as an area in which the memory cells 43 shown in FIG. 3D are repeated, a layout of the memory mat 42 is specified in a rectangular form. As an area in which the memory mats 42 (rectangles) shown in FIG. 3C are repeated, the memory mat group 41 is set.

Figure 5A:
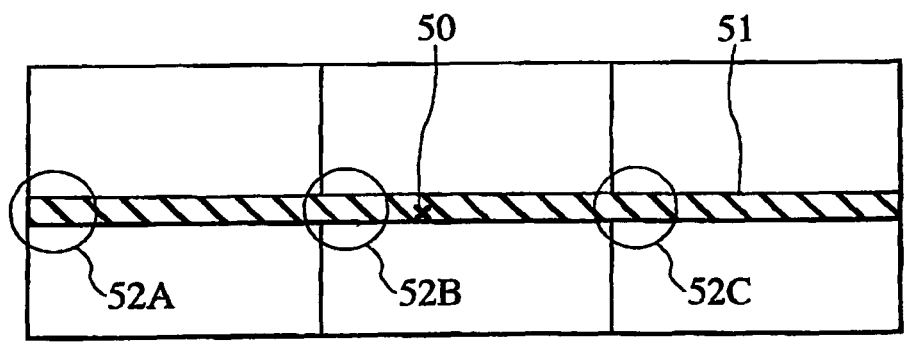
FIGS. 5A, 5B are diagrams each illustrating image processing performed in trial inspection.
Figure 5B:
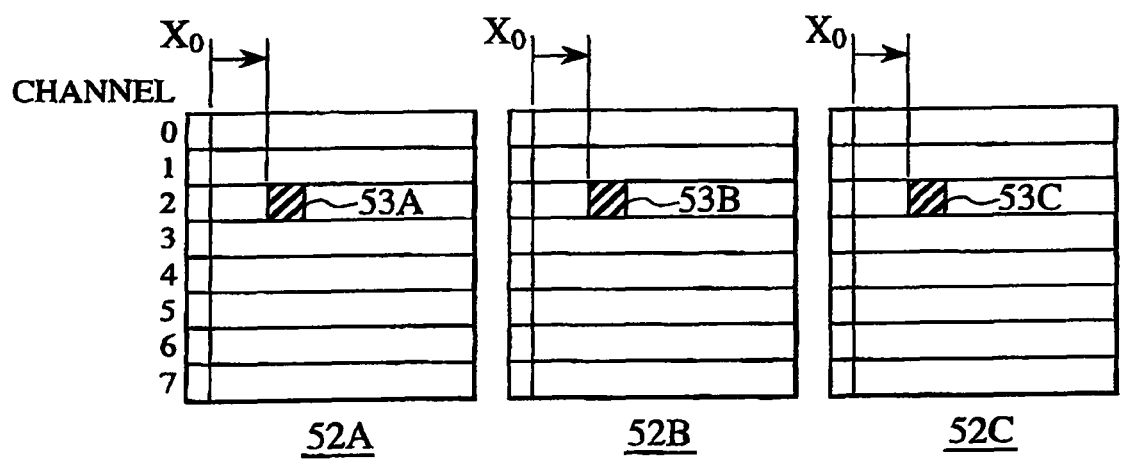

Next, trial inspection is performed to check whether or not setting conditions are correct (step 407). FIGS. 5A, 5B are diagrams each illustrating image processing of the trial inspection. FIG. 5A is a plan view schematically illustrating dies; and FIG. 5b is a diagram schematically illustrating data storage areas of the image memory 30. The operation of the trial inspection will be described with reference to FIGS. 5A, 5B. An elongated rectangular area which has the moving length equivalent to three dies, the central one of which is a specified die, and which has the width along which the deflector 3 shown in FIG. 1 can perform scanning, is designated as a stripe area 51. The stripe area 51 is indicated with oblique lines. The operator specifies trial-inspection coordinates 50 at which trial inspection is to be performed. The total control unit 18 shown in FIG. 1 moves the XY stage 7 in the stripe area 51 including the trial-inspection coordinates 50, and controls the deflector 3 to perform scanning in synchronization with the move. Thus, the secondary signal 10 generated in the semiconductor wafer 6 is detected by the sensor 13. At this time, a focus position is corrected by controlling an excitation current value of the objective lens 4 based on the height of the semiconductor wafer 6 detected by the height sensor 8. An analog signal detected by the sensor 13 is converted into the digital signal 14 by the A/D converter 15. Based on the digital signal 14, the defect judgment unit 17 then judges the defect information 16 that is information about whether or not a defect exists. The judged defect information 16 is temporarily stored in a storage unit (not illustrated) provided in the total control unit 18. The distribution of defects associated with the defect information 16 is displayed in a map format on the console 19.

The defect judgment unit 17 operates in the steps described below. Specifically, the digital signal 14 obtained from the stripe area 51 shown in FIG. 5 is stored in the image memory 30 shown in FIG. 2 on a die basis. The stored data is divided into, for example, eight channels, each of which has a width of 128 pixels. Data of a specified area in a die is stored in the same area of each channel of the image memory 30 in a one-to-one correspondence manner by use of the image averaging technique (more specifically, FR-RIA (Full Region-Reference Image Averaging)) that uses the repeatability of memory cells of the image memory 30, which is described in the non-patent literature 1. The image distribution unit 31 distributes pieces of image data 53A, 53B, 53C in association with areas 52A, 52B, 52C based on the same PE32 respectively. Each of the pieces of image data 53A, 53B, 53C starts from a location that deviates by a constant value (X0) in each channel corresponding to coordinates in each die. Each of the pieces of image data 53A, 53B, 53C has the length equivalent to 128 lines. Here, if there is no defect in the specified area, an image of the specified area in the die is the same as that of an area in another die corresponding to the same die coordinates as those of the specified area. Thus, if there is no defect for the image of the specified area having the same die coordinates, a defect is not detected even if differences between images are calculated. If any one of three specified areas has a defect, there is a difference in image data between two of the three specified areas. Therefore, image data containing a defect can be found by comparing two pieces of image data corresponding to two of the three specified areas in all combinations.

Figure 6A:
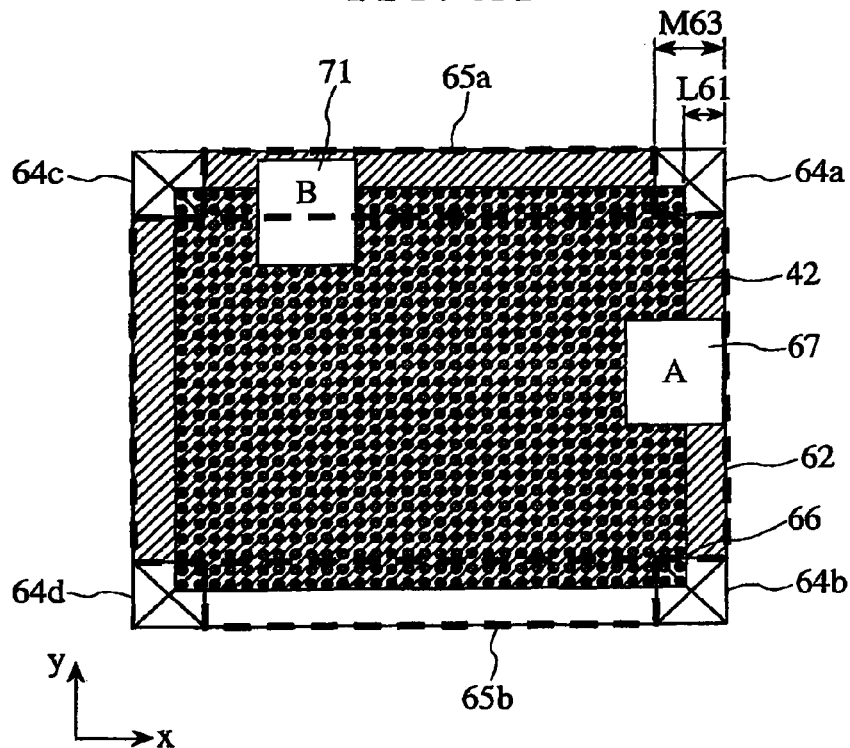
FIGS. 6A, 6B are diagrams each illustrating a FR-RIA (Full Region-Reference Image Averaging) technique.
Figure 6B:
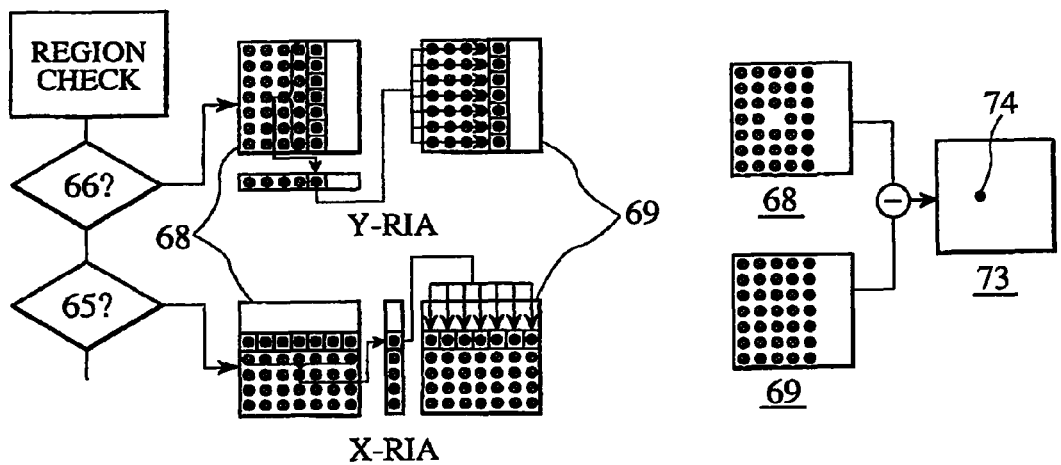

FIGS. 6A, 6B are diagrams illustrating the FR-RIA technique. FIG. 6A is a plan view illustrating the memory mat 42 shown in FIG. 3; and FIG. 6B is a flowchart that uses part of the plan view. An area 62 is a portion enlarged by L 61 from a rectangular area that defines the memory mat 42, and another area is a portion reduced by M 63 from the area 62. L 61 indicates an upper limit by which a set area may deviate. It is assumed that the size of M 63 is twice the size of L 61. The area 62 can be divided into three kinds of areas. Specifically, the three kinds of areas are as follows: corner areas 64*a*, 64*b*, 64*c*, 64*d*, each of which starts from each corner of the area 62, and each of which has the size M 63; top and bottom end areas 65*a*, 65*b* that touch the top and bottom sides respectively, the width of the top and bottom end areas 65*a*, 65*b* being defined by the size M 63; and other areas 66. In each of the corner areas 64*a*, 64*b*, 64*c*, 64*d*, there is a possibility that each corner of the memory mat 42 will move to an optional position in each area due to the area's deviation. The corner areas 64*a*, 64*b*, 64*c*, 64*d*, therefore, are areas in which the repeatability cannot be expected. The top and bottom end areas 65 are areas in which the repeatability can be expect at least in the X direction. The other areas 66 are areas in which the repeatability can be expected in the Y direction.

If a detected image 68 having a size of "128 pixels×128 lines", which has been distributed to the PE 32, is an area A67, all pixels of the distributed images have the repeatability in the Y direction. For this reason, an image combined by adding and averaging images by pitch repeated in the Y direction is created, and the image combined by the addition and averaging is then reallocated to generate an averaged image 69. This is Y-RIA processing. The Y-RIA processing is the FR-RIA processing limited in the Y direction. If a detected image 68 having a size of "128 pixels×128 lines", which has been distributed to the PE 32, is an area B71, all pixels of the distributed images have the repeatability in the X direction. For this reason, an image combined by adding and averaging images by pitch repeated in the X direction is created, and the image combined by the addition and averaging is then reallocated to generate an averaged image 69. This is X-RIA processing. The X-RIA processing is the FR-RIA processing limited in the X direction. Calculation is performed for obtaining a difference image 73 as a difference between the detected image 68 and the averaged image 69. Based on the calculated value of the difference image 73, an area associated with a value larger than a set defect-judgment threshold value is judged to have a defect 74.

Figure 7:
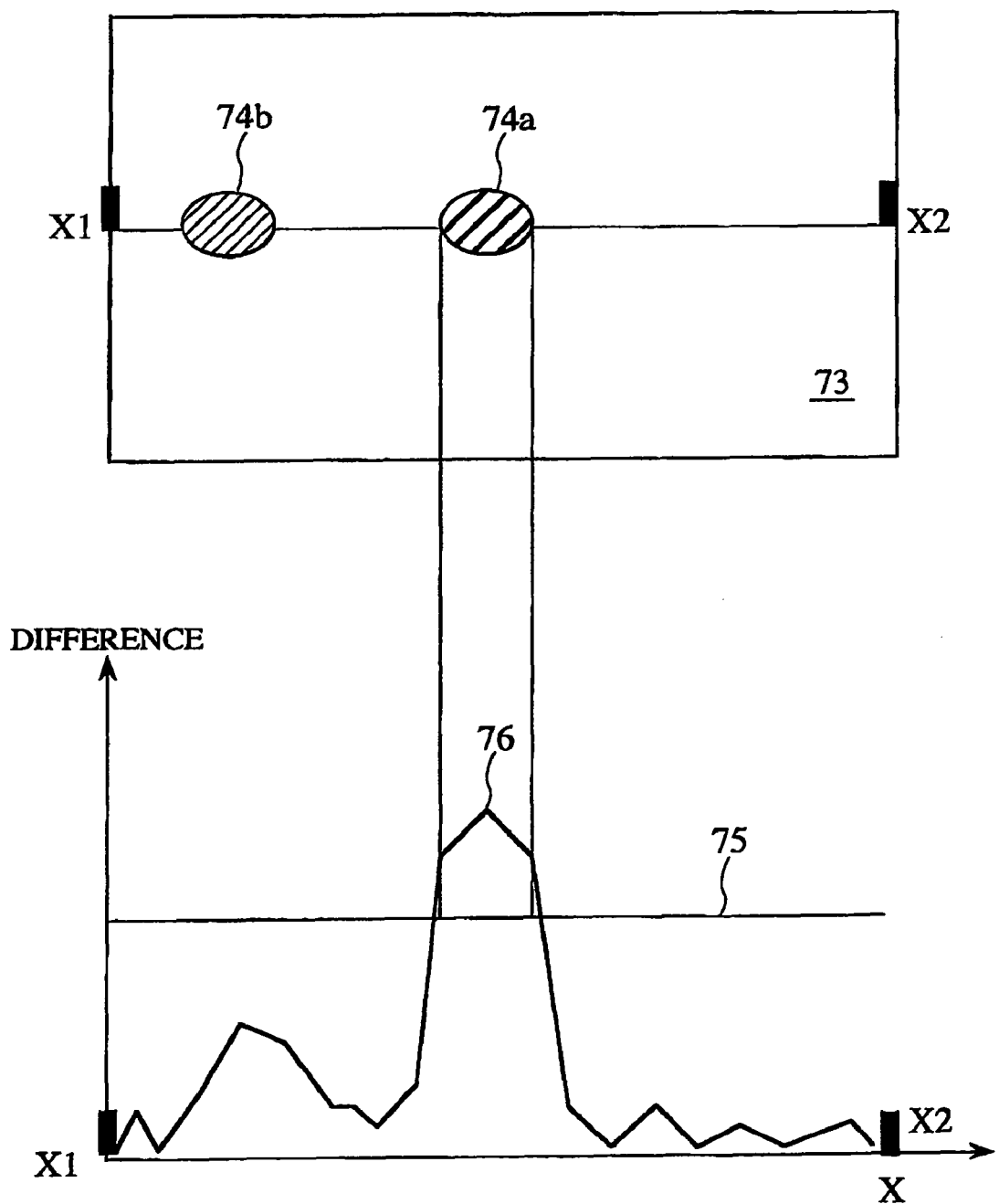
FIG. 7 is a graph illustrating a difference image and the difference used to explain the calculation of the difference.

FIG. 7 is a graph illustrating the difference image 73 and the difference. This graph is used to explain the calculation of the difference. The calculation of the difference will be described below with reference to FIG. 7. It is assumed that the difference image 73 includes two areas: a defect 74*a*; and an area 74*b* for which the difference is large although the latter area is not defective. In FIG. 7, each difference value across a cross section X1-X2 is shown in the graph. Each pixel of a detected image is expressed by a gray scale value from black to white. A vertical axis indicates a difference in the gray scale value of the detected image. An area having a difference value 76 larger than a predetermined defect-judgment threshold value 75 is judged to be defective. A position of the defect 74*a*, i.e., XY coordinates and information about the difference value 76 are output as partial defect information 33 shown in FIG. 2. Thus, it becomes possible to judge whether or not a defect exists in areas included in the area 62 shown in FIG. 6 (excluding the corner areas 64*a*, 64*b*, 64*c*, 64*d*).

Figure 8:
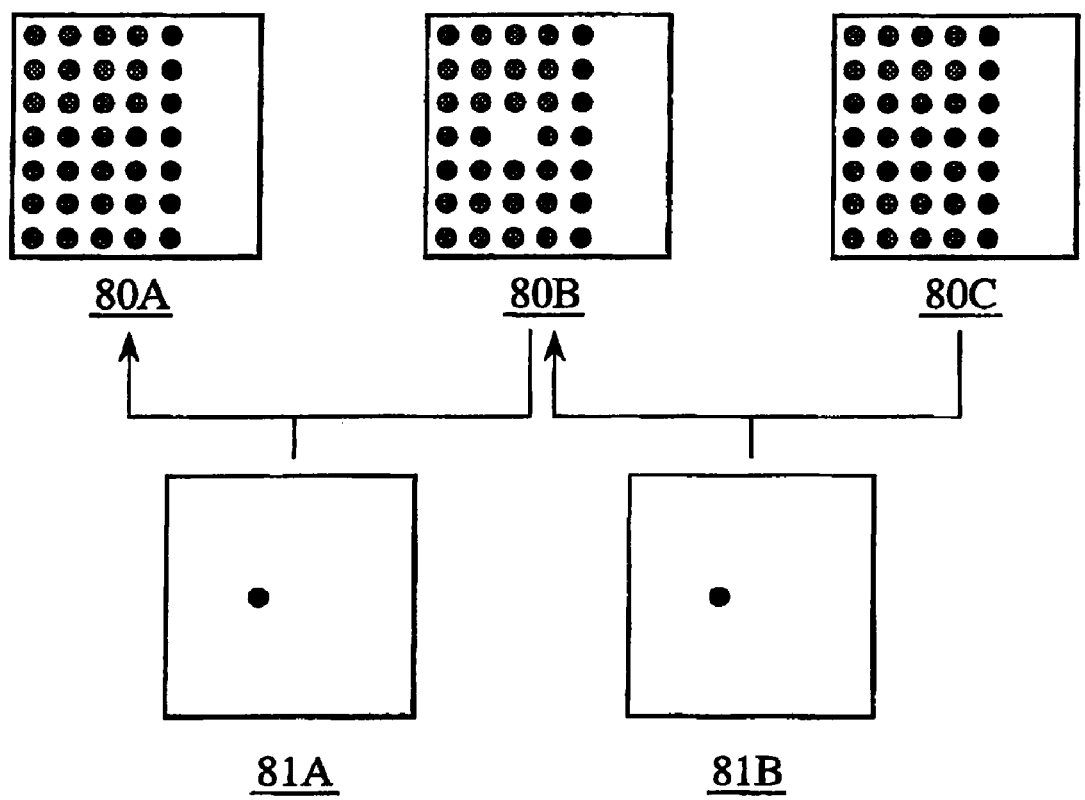
FIG. 8 is a flowchart that uses part of the plan view of a memory mat shown in FIG. 3.

An example of defect judgment based on the die comparison will be described with reference to FIG. 8. FIG. 8 is a flowchart that uses part of the plan view of the memory mat 42 shown in FIG. 3. For three dies that are adjacent to one another in succession, the difference in image data between memory mat areas having the same coordinates is calculated. Specifically, three detected images 80A, 80B, 80C of three successive dies are distributed to the same PE 32. Each of the detected images 80A, 80B, 80C is spaced away from each die origin point by the distance $X_0$, and has a size of "128 pixels× 128 lines". The distribution is performed as described in FIG. 5. A difference image 81A between the detected image 80A and the detected image 80B, and a difference image 81B between the detected image 80B and the detected image 80C, are calculated. As described in FIG. 7, Based on the calculated values of the difference images 81A and 81B, an area associated with a value larger than a set defect-judgment threshold value is judged to have a defect. In the example shown in FIG. 8, because a defect is detected in both of the difference images 81A, 81B, it is found out that a defect exists in the detected image 80B. The result of the judgment is output as the partial defect information 33 shown in FIG. 2.

The information integration unit 34 shown in FIG. 2 aggregates the partial defect information 33 transmitted from all of the PEs 32, and then outputs information judged by either the FR-RIA processing or the die comparison as defect information 16.

FIGS. 9A, 9B are diagrams each illustrating, as an example of GUI, a screen in which defect information is displayed. On the left side of the screen shown in FIG. 9A, a plurality of schematic diagrams each corresponding to an image of the stripe area 51 shown in FIG. 5 are displayed in the longitudinal direction. This screen area is designated as a stripe map 90. This stripe map 90 is a schematic diagram that is generated for reasons of convenience to indicate not a detected image and a difference image, but a position of a defect. A position of the detected defect 74 is displayed in a symbolized manner in the stripe map 90. On the right side of the screen shown in FIG. 9A, an image display area 91 is provided. A detected image, a reference image, and a difference image, all of which are associated with the defect 74, are displayed by specifying (for example, clicking) a symbol of the defect 74. By averaging images by use of the above-described FR-RIA technique, noises included in the detected image and the reference image are reduced and the difference between images each containing little noise is calculated. This makes it possible to acquire a difference image from which a defect can be easily identified. A defect-information display area is provided adjacently to the image display area 91. In connection with a defect displayed in the image display area 91, information including coordinates, a projected length, a difference value, a difference in gray scale, and the quantity of background light are numerically displayed. In addition, when a defect is automatically classified, or when an operator inputs the classification thereof, the corresponding classification is displayed. Because a shape or color of the symbol of the defect 74 displayed in the stripe map 90 is changed according to the classification thereof, the operator can visually immediately know the classification of the defect.

Because the defect judgment shown in FIG. 7 is based on arithmetic processing that uses the detected image, the defect-judgment threshold value 75 of the difference value can be changed, and the result can be displayed on the screen shown in FIG. 9. Specifically, the operator can change the defect-judgment threshold value 75 by using a display threshold-value adjustment toolbar 93.

After the fixed quantity of data is classified, the display threshold-value adjustment toolbar 93 is used to change the display threshold value so that only defects each having a difference value which is larger than or equal to the display threshold value are displayed. When the threshold value is changed using the display threshold-value adjustment toolbar 93 before inspection, only defects which are displayed on the screen can be detected. Therefore, a correct threshold value can be easily known. If a pattern having a pitch whose length is, for example, four times the pitch of the memory mat exists in a circumferential part of the memory mat, and if a normal portion in this portion is judged to be defective, a judgment condition setting tab is selected to display a judgment condition setting area 94. Next, according to the situation, the size of M is changed or in the case of the inside of the size of M, the pitch magnification of the repeated pitch with respect to the inside of the memory mat is changed for correct settings.

Returning to FIG. 4A, the steps will be further described. The inspection conditions are checked by the above-described work (step 408). A judgment is then made as to whether or not the inspection conditions are satisfied (step 409). If it is judged that the inspection conditions are not satisfied, the process return to the step 406. In contrast, if it is judged that the inspection conditions are satisfied, reference accumulation information is determined, and the check work is ended (step 410). The recipe is then stored, and the semiconductor wafer is unloaded from the circuit-pattern inspection apparatus before the creation of the recipe is completed (step 411).

Next, inspection steps will be described with reference to FIG. 4B. Inspection is performed according to the recipe that has been created in the steps shown in FIG. 4A. When an operator instructs, through the console 19, the total control unit 18 to execute the inspection, the total control unit 18 selects a recipe suitable for attributes of the semiconductor wafer 6 that is a target to be inspected, and then loads the recipe into a calculation memory (not illustrated) of the microprocessor of the total control unit 18 (step 412). The semiconductor wafer 6 is loaded into the circuit-pattern inspection apparatus, and is then placed on the sample stage 9 (step 413).

Conditions of an optical system are set for the electron source 11, the deflector 3, the objective lens 4, the charge control electrode 5, the converging optical unit 12, the sensor 13, and the A/D converter 15 (step 414). An image of the standard sample piece 21 is detected, and the detected image is then properly corrected on the basis of the recipe. The semiconductor wafer 6 is aligned under the conditions set in the recipe (step 415) to acquire an image used for calibration. Image acquisition conditions such as a gain of the sensor 13 are set so that the proper light quantity is achieved to prevent the light quantity from becoming insufficient or excessive (step 416).

Next, an inspection area specified by the operator beforehand is subjected to image detection and defect judgment. More specifically, the defect judgment is then performed as follows. On the basis of setting conditions of the recipe, the deflector 3 is controlled to perform scanning in synchronization with the move of the XY stage 7, so that the sensor 13 detects the secondary signal 10 generated from the semiconductor wafer 6. At this time, a focus position is corrected by controlling an excitation current value to be applied to the objective lens 4 on the basis of the height of the semiconductor wafer 6 detected by the height sensor 8. An analog signal which has been detected by the sensor 13 is converted into the digital signal 14 by the A/D converter 15 to acquire a detected image. A difference image is generated, from the acquired detected image, according to the steps similar to those in the trial inspection performed when the recipe is created, thereby determining a difference value (step 417). Every time a defect is detected, a defect signal is accumulated, detected defects are selected, a judgment is made as to whether or not the particular defect is a real defect, and the classification for the defects judged is performed (step 418). The defect information 16, which is the result of the defect judgment, is stored in a storage unit (not illustrated) together with the inspection conditions (step 419). The semiconductor wafer 6 is then unloaded before the inspection is ended (step 420).

In the example shown in FIG. 6, the inspection area is divided into three kinds of areas: the corner area 64, the top and bottom end area 65, and the other area 66. However, the inspection area may also be divided into four kinds of areas. Specifically, the other area 66 is divided into: an area which starts from the circumference of the area 62 and ends at a position that is spaced away from the circumference of the area 62 by the size of M; and the other area. The area, which starts from the circumference of the area 62 and ends at the position spaced away from the circumference of the area 62 by the size of M, has the repeatability only in the Y direction. In contrast, the other area has the repeatability in two directions of the X direction and the Y direction. When the addition operation has the repeatability in the two directions, two-directional repeatability is used to perform the addition and averaging. This makes it possible to reduce a noise component, and to achieve the inspection with higher sensitivity.

According to the first embodiment of the present invention described above, the defect judgment is performed by use of the FR-RIA technique with each corner portion of the memory mat excluded. Therefore, the influence of noises caused when a difference image is generated can be minimized. This makes it possible to perform the defect judgment of an area including the circumference of the memory mat with extremely high sensitivity. Moreover, the whole surface of each die, which includes each corner portion of a memory mat, and circuits located in the circumference, can be inspected by combining the result provided by the above-described defect judgment with the result of the defect judgment based on the comparison between dies. Thus, an outstanding effect that the present embodiment exhibits is that there is no area that cannot be subjected to inspection.

Second Embodiment

Next, a second embodiment of the present invention will be described with reference to accompanying drawings. The overall configuration of a circuit-pattern inspection apparatus is the same as that of the circuit-pattern inspection apparatus described in the first embodiment. In addition, a defect judgment unit and inspection steps are also the same as those of the first embodiment. Therefore, only differences between the first and second embodiments will be described below.

Figure 10A:
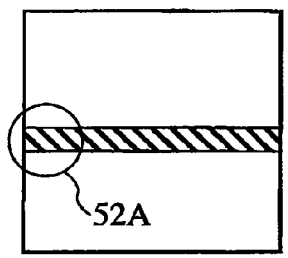
FIGS. 10A through 10C are diagrams each illustrating image processing performed in trial inspection.
Figure 10B:
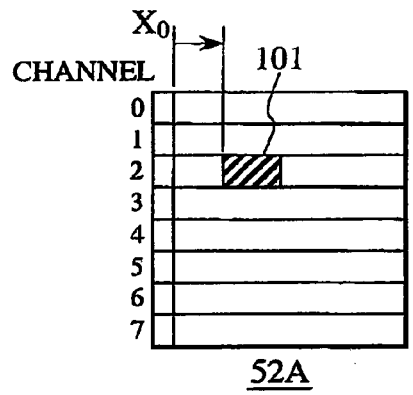
Figure 10C:
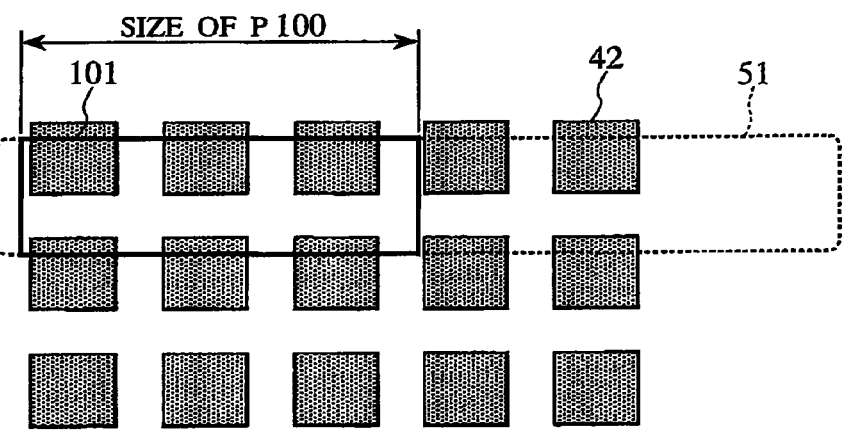

As is the case with FIGS. 5A, 5B, FIGS. 10A, 10B, 10C are diagrams each illustrating image processing of trial inspection. FIG. 10A is a plan view schematically illustrating a die; FIG. 10B is a diagram schematically illustrating a data storage area of the image memory 30; and FIG. 10C is a diagram schematically illustrating an image acquisition unit of a stripe area. First, like in FIGS. 5A and 5B, the trial-inspection coordinates 50 at which trial inspection is to be performed is specified. The XY stage 7 is then moved in the stripe area 51 including the trial-inspection coordinates 50 so as to acquire an image signal. The defect judgment unit 17 shown in FIG. 1 stores the digital signal 14 indicative of the stripe area 51 in the image memory 30 shown in FIG. 2. The stored data is divided into eight channels, each of which has a width of 128 pixels. Based on a two-directional cell comparison technique that makes use of the repeatability of memory cells of the image memory 30, data of a specified area in a die is stored in the same area of each channel of the image memory 30 in a one-to-one correspondence manner. The image distribution unit 31 shown in FIG. 2 extracts image data 101 having a length of the size of P 100, which covers three memory mats 42, from the stripe area 51 shown in FIG. 10C. The image distribution unit 31 then distributes the image data 101 to the PE 32. Pitch of the size P 100 is made to coincide with that of the memory mat 42. This is performed for the areas 52A, 52B, 52C of each adjacent die as shown in FIGS. 5A, 5B. Here, if there is no defect in the specified area, an image of the specified area in the die is the same as that of an area in another die corresponding to the same die coordinates as those of the specified area. Thus, if there is no defect for the image of the specified area having the same die coordinates, a defect is not detected even if differences between images are calculated. Therefore, image data containing a defect can be found by comparing two pieces of image data corresponding to two of the three specified areas in all combinations.

Figure 11A:
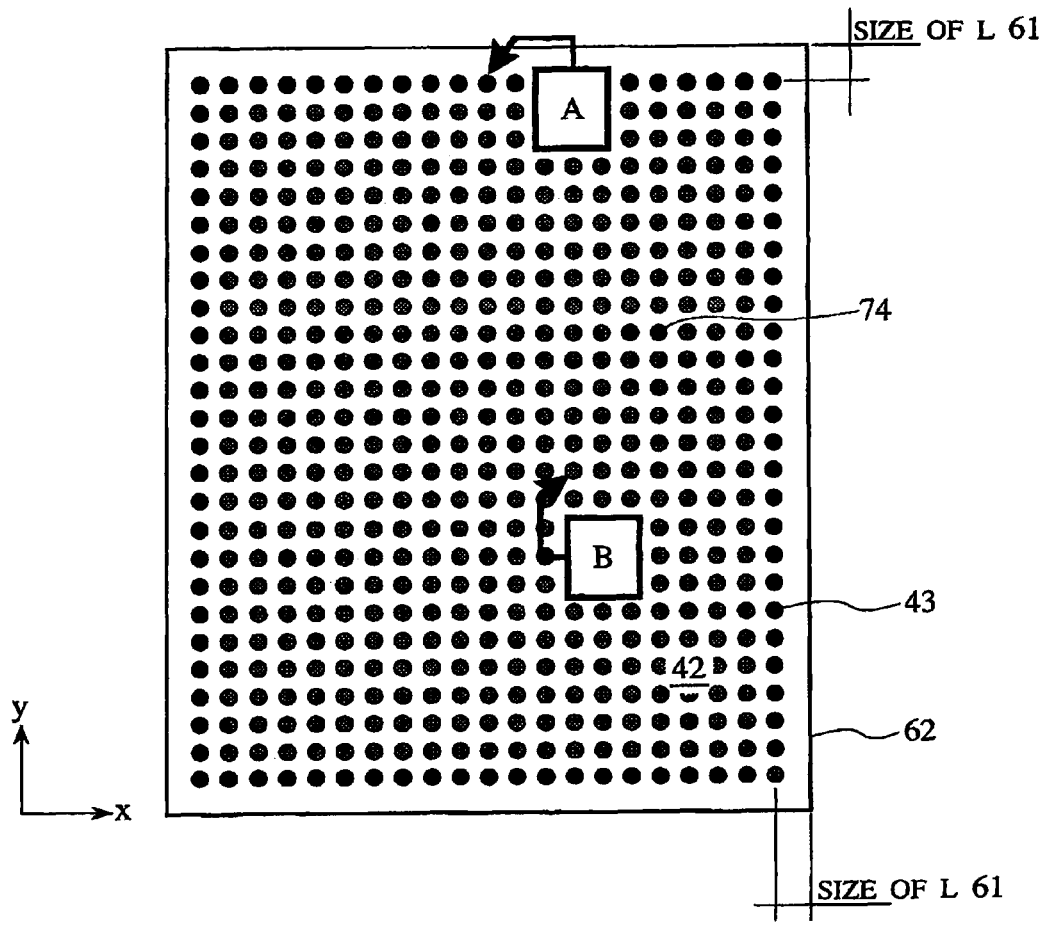
FIGS. 11A, 11B are plan views each illustrating a memory mat of a die used to explain a two-directional cell comparison technique.
Figure 11B:
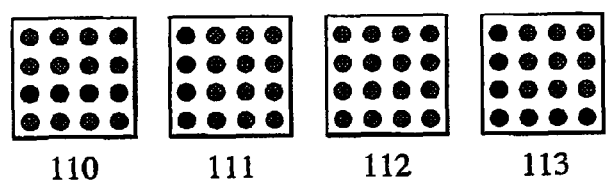

FIGS. 11A, 11B are plan views each illustrating a memory mat of a die. FIGS. 11A, 11B are used to explain a two-directional cell comparison technique. An area 62 is a portion enlarged by the size of L 61 from a rectangular area that defines the memory mat 42 in which the memory cells 43 are arrayed. Reference numeral 74 shown in the figure denotes a defect. The size L 61 indicates an upper limit by which a set area may deviate. A detected image having a size of "128 pixels×128 lines" obtained by dividing "128 pixels×P lines" distributed to the PE 32 can be classified into four kinds of patterns (patterns 110, 111, 112, 113). Specifically, the pattern 110 is an X-direction repeated pattern that has the repeatability in the X direction, and that does not have the repeatability in the Y direction; the pattern 111 is a Y-direction repeated pattern that has the repeatability in the Y direction, and that does not have the repeatability in the X direction; the pattern 112 is a non-repeated pattern that does not have the repeatability in both the X direction and the Y direction; and the pattern 113 is an XY-direction repeated pattern that has the repeatability in both the X direction and the Y direction. Therefore, a reference image to be compared is selected on the basis of the repeatability of each pattern.

According to this embodiment, one image includes four memory cells 43. On the assumptions that the size corresponding to a pitch that is four times the repeated pitch of a memory cell in the X direction is Qx, and that the size corresponding to a pitch that is four times the repeated pitch of the memory cell in the Y direction is Qy, an area A shown in FIG. 11A corresponds to a pattern 110. Accordingly, an X-directional pattern whose size is equivalent to the repeated pitch Qx is compared as a reference image. For an area B (FIG. 11A) corresponding to patterns 111, 113, a Y-directional pattern whose size is equivalent to the repeated pitch Qy is compared as a reference image. The pattern 112 may also be compared as a reference image in both X and Y directions.

Figure 12:
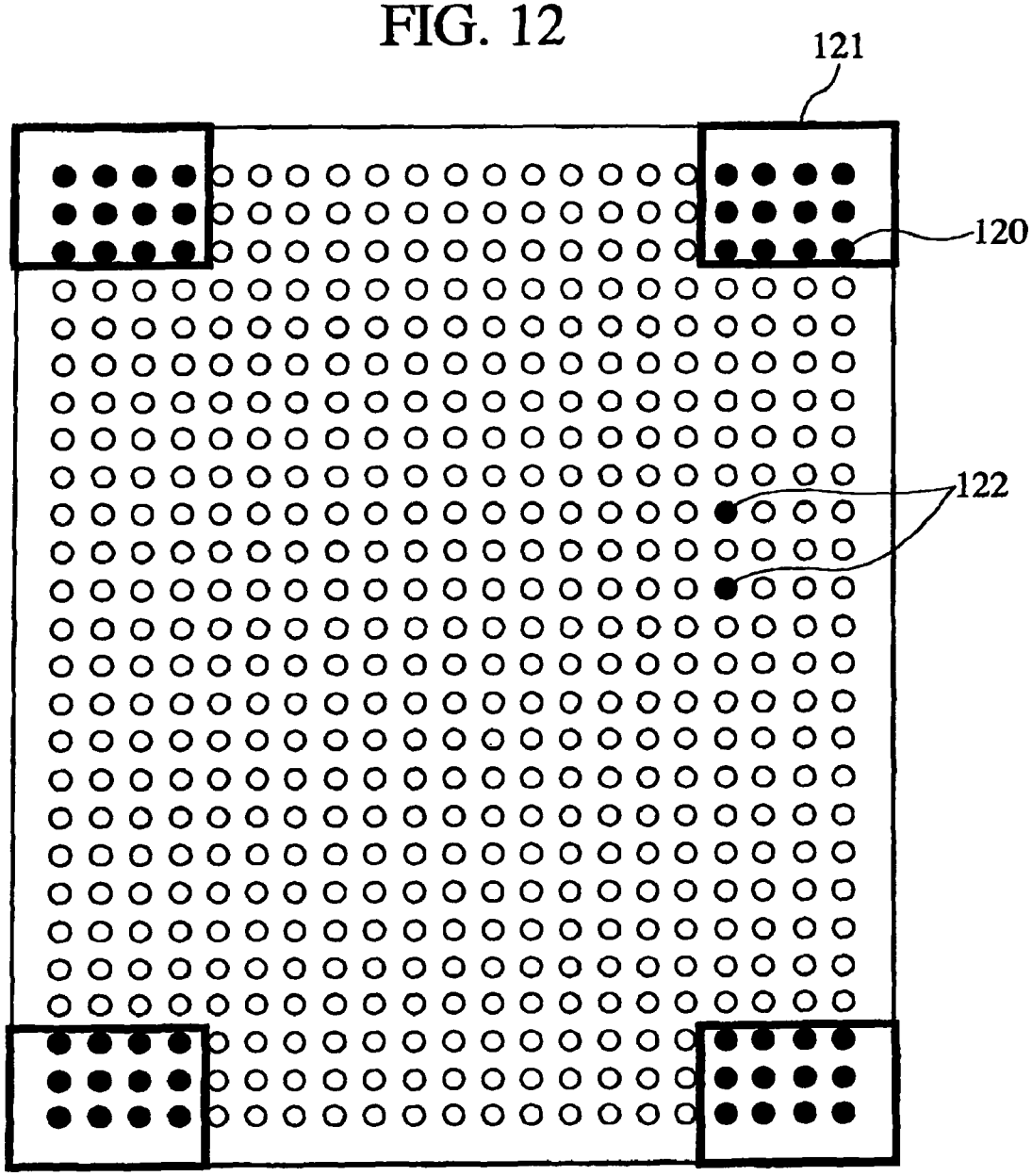
FIG. 12 is a plan view illustrating a memory mat of a die.

Similar to FIG. 11, FIG. 12 is a plan view illustrating a memory mat of a die. In an area 121 that is a corner portion, because a comparison is made with a pattern that cannot be primarily compared, the difference becomes large in an area 120 although the area 120 is non-defective. The area 120 whose difference is large exists inside the corner area 121 whose X-directional size is L+Qx from the corner, and whose Y-directional size is L+Qy from the corner. If an area whose difference is large exists in the corner area 121, this area is not judged to be defective. On the other hand, real defects 122 which are not included in the area 121 are output as partial defect information 33.

Figure 13:
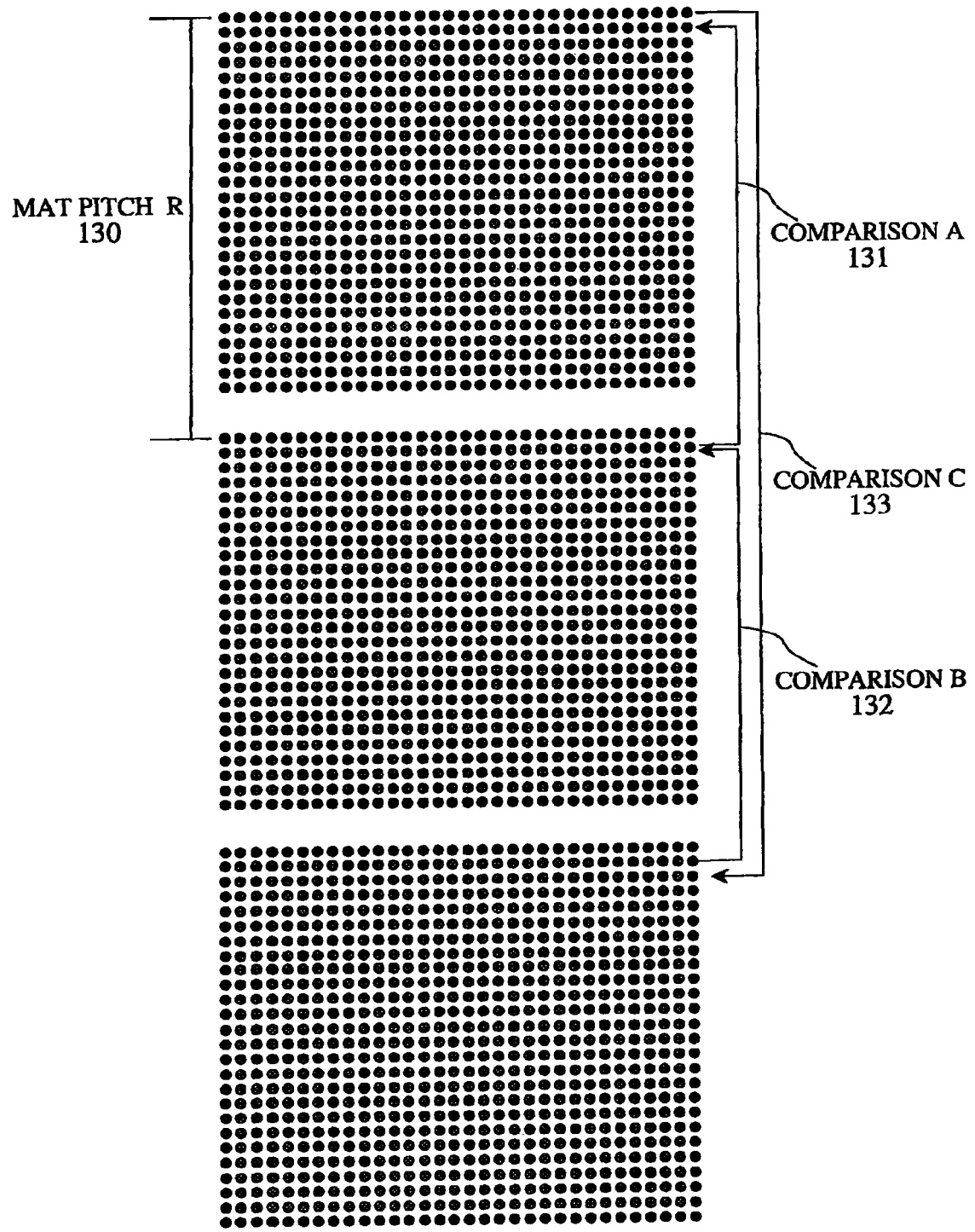
FIG. 13 is a plan view illustrating a memory mat of a die.

FIG. 13 is a plan view illustrating memory mats of a die. Steps of mat comparison (comparison of memory cells) will be described with reference to FIG. 13. When image data is distributed to the image memory 30 shown in FIG. 2, three-memory mat image data are distributed to the PE 32 with reference to mat pitch R130. If patterns of the image data have no defect, these patterns are identical to one another. Accordingly, memory cells can be compared by comparing same positions in three pieces of the image data. Specifically, as shown in FIG. 13, comparison is made by the PE 32 for a comparison A 131, a comparison B 132, and a comparison C 133 associated with each other as shown by respective arrows. After that, as shown in FIG. 7, an image having a difference value which is larger than or equal to the defect-judgment threshold value 75 is judged to be a defect, and the result of the judgment is then output as the partial defect information 33.

The information integration unit 34 shown in FIG. 2 aggregates the partial defect information 33 transmitted from all of the PEs 32, and then outputs, as defect information 16, information about the defect judged by either the two-directional cell comparison or the mat comparison. A GUI screen for displaying the output defect information and the operation of setting inspection conditions are the same as those described in the first embodiment. Therefore, description thereof will be omitted.

According to the second embodiment of the present invention, the defect judgment can be performed by use of the two-directional cell comparison technique except each corner portion of a memory mat. This makes it possible to perform the defect judgment of the memory mat up to the circumference thereof. Moreover, because the result of the defect judgment based on the two-directional cell comparison is output together with the result of the defect judgment based on the mat comparison, the whole surface of the memory mat including corner portions of the memory mat can be inspected.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A circuit-pattern inspection apparatus that acquires an image of a circuit pattern of a die formed on a semiconductor wafer to judge whether or not the circuit pattern has a defect, the apparatus comprising:
   a plurality of image memories, each of which stores data of the image distributed on the basis of the repeatability of the circuit pattern;
   a plurality of processor elements that determine a direction of the repeatability of the circuit pattern, wherein each processor element compares the image data stored in a respective one of the image memories with a reference image generated by adding and averaging in the direction of the repeatability to generate a difference image, and judges whether an area, in which a difference value of the difference image is larger than a predetermined threshold value, is a defect; and
   an information integration unit for integrating and outputting a plurality of pieces of defect information, the defect information including image data judged to be defective by one of the processor elements and coordinates indicative of the defect.

2. A circuit-pattern inspection apparatus that acquires an image of a circuit pattern of a die formed on a semiconductor wafer to judge whether or not the circuit pattern has a defect, the apparatus comprising:
   a plurality of image memories, each of which stores data of the image distributed on the basis of the repeatability of the circuit pattern;
   a plurality of processor elements, wherein each processor element compares the image data stored in a respective one of the image memories with a reference image combined by adding and averaging in a direction of the repeatability to generate a difference image, and judges that an area in which a difference value of the difference image is larger than a predetermined threshold value is a defect; and an information integration unit for integrating and outputting a plurality of pieces of defect information, the defect information including image data judged to be defective by one of the processor elements and coordinates indicative of the defect, wherein:

when a memory cell is judged to be defective in a corner portion of a rectangular area of a memory mat having a plurality of memory cells in the circuit pattern of the die, one of the processor elements does not treat the memory cell as a defect, the reference image is at least an image of a different memory mat or an image of a different die, and a target area where a defect is detected is the whole surface of the memory mat including each corner portion of the rectangular area of the memory mat.

3. A circuit-pattern inspection method in which an image of a circuit pattern of a die formed on a semiconductor wafer is acquired to judge whether or not the circuit pattern has a defect, the method comprising steps of:

on the basis of the repeatability of the circuit pattern, distributing data of the image to a plurality of image memories and storing the data therein;

determining a direction of repeatability of the circuit pattern;

comparing the image data stored in each of the image memories with a reference image generated by adding and averaging in the direction of the repeatability to generate a difference image;

judging that an area in which a difference value of the difference image is larger than a predetermined threshold value is a defect; and integrating and outputting a plurality of pieces of defect information, the defect information including image data judged to be defective and coordinates indicative of the defect.

4. A circuit-pattern inspection method in which an image of a circuit pattern of a die formed on a semiconductor wafer is acquired to judge whether or not the circuit pattern has a defect, the method comprising steps of:

on the basis of the repeatability of the circuit pattern, distributing data of the image to a plurality of image memories and storing the data therein;

comparing the image data stored in each of the image memories with a reference image combined by adding and averaging in a direction of the repeatability to generate a difference image;

judging that an area in which a difference value of the difference image is larger than a predetermined threshold value is a defect; and integrating and outputting a plurality of pieces of defect information, the defect information including image data judged to be defective and coordinates indicative of the defect, wherein:

when a memory cell is judged to be defective in a corner portion of a rectangular area of a memory mat having a plurality of memory cells in the circuit pattern of the die, the memory cell is not treated as a defect, the reference image is at least an image of a different memory mat or an image of a different die, and a target area where the defect is detected is the whole surface of the memory mat including each corner portion of the rectangular area of the memory mat.

* * * * *